United States Patent [19]
Sato et al.

[11] Patent Number: 4,715,218
[45] Date of Patent: Dec. 29, 1987

[54] METHOD OF DETERMINING DEGREE OF EMBRITTLEMENT OF LOW ALLOY STEEL

[75] Inventors: Noriko Sato, Tokyo; Masayuki Suzuki, Yokohama, both of Japan

[73] Assignee: Kabushiki Kaisha Toshiba, Kawasaki, Japan

[21] Appl. No.: 890,281

[22] Filed: Jul. 29, 1986

[30] Foreign Application Priority Data

Mar. 25, 1986 [JP] Japan ............................... 61-64707

[51] Int. Cl.⁴ ..................... G01N 17/00; G01N 27/00
[52] U.S. Cl. ................................... 73/86; 324/71.2; 204/1 T; 204/404
[58] Field of Search ............... 73/86, 78, 87; 324/71.1, 71.2; 204/1 T, 404

[56] References Cited

U.S. PATENT DOCUMENTS

| | | | |
|---|---|---|---|
| 3,228,236 | 1/1966 | Landrum et al. | 73/86 |
| 3,466,238 | 9/1969 | Mahieu et al. | 204/404 |
| 4,064,438 | 12/1977 | Alex et al. | 250/358.1 |
| 4,518,464 | 5/1985 | Takahashi et al. | 204/404 |

FOREIGN PATENT DOCUMENTS

| | | | |
|---|---|---|---|
| 0014155 | 1/1985 | Japan | 324/71.1 |
| 0056251 | 4/1985 | Japan | 324/71.1 |
| 0986973 | 1/1983 | U.S.S.R. | 204/1 T |

Primary Examiner—Stewart J. Levy
Assistant Examiner—Robert R. Raevis
Attorney, Agent, or Firm—Oblon, Fisher, Spivak, McClelland & Maier

[57] ABSTRACT

A method of determining the degree of embrittlement of low alloy steel with high accuracy and good reproducibility, comprising the steps of bringing the low alloy steel into contact with an aqueous solution of an aromatic compound having a nitro group and at least one of a hydroxyl group and a carboxyl group, measuring an open circuit potential of the steel, and determining the degree of embrittlement of the low alloy steel caused by the thermal history of the low alloy steel using the measured value.

24 Claims, 11 Drawing Figures

FIG. 11

METHOD OF DETERMINING DEGREE OF EMBRITTLEMENT OF LOW ALLOY STEEL

BACKGROUND OF THE INVENTION

I. Field of the Invention

The present invention relates to a method of determining the degradation of low alloy steel and, more particularly, to a method of nondestructively measuring the degree of degradation of low alloy steel, embrittled in a high temperature atmosphere over a long period of use, using an electrochemical measurement.

II. Description of the Prior Art

A metallic material, such as steel, is given various heat treatments to obtain the mechanical property required for its application, and is then used. However, in a material which is used at a comparatively high temperature of several hundreds degrees centigrade, the mechanical property is degraded. Although such degradation in the mechanical property is often due to creep deformation caused by a regular stress, it is sometimes based on various textural changes.

For example, in a rotor of a steam turbine which operates at a high temperature, phosphorus as an impurity in steel segregates at crystal grain boundaries, thereby weakening the grain boundary strength. As a result, the toughness of the steel is significantly lowered, i.e., temper embrittlement occurs. Observation through a microscope or using a Charpy impact test is the most direct method of determining the degree of degradation of such a metallic material. These methods are accurate determining methods, but they have a big disadvantage in that extracting a test specimen from the metallic member is required.

In view of the foregoing, a nondestructive test method of electrochemically detecting a textural change in the metallic material has recently been developed. In the above conventional methods, a metallic material to be tested is used as a working electrode to be brought into contact with an appropriate electrolytic solution. A reference electrode and auxiliary electrode are dipped into the same electrolytic solution, and a polarization property is measured by these electrodes, thereby detecting a textural change in the metallic material by an appropriate parameter obtained by this measurement or by comparison of the obtained parameter with that of a virgin metallic material. In this case, as a parameter, an anodic or cathodic peak current density of a polarization curve, a critical pitting potential, a repassivation potential, a passivation current density, a charge quantity flowing in a potential range of interest, and a ratio of parameters during normal potential sweep and reverse sweep may be used.

These measurements, however, of polarization behavior generally have poor reproducibility. Though conventional methods have been improved to compensate for this defect, because of the large scattering in measured values, it is difficult to obtain a clear relationship between the measured values and the degree of embrittlement of a metallic material. In addition, when an electrochemical measurement of the degree of embrittlement of a metallic material is performed, the selection of an electrolytic solution is an important problem. Nevertheless, sufficient studies and developments have not been made concerning such solutions, and a method of determining the brittleness of a metallic material with high accuracy has not yet been provided.

SUMMARY OF THE INVENTION

It is an object of the present invention to provide a method of determining, with high accuracy and good reproducibility, the degree of embrittlement of low alloy steel used at high temperatures.

The present inventors found that when low alloy steel, such as Cr-Mo steel or Cr-Mo-V steel, was placed in a specific aqueous acid solution, an open circuit potential of the low alloy steel had a linear relationship with the degree of embrittlement, which is caused by its thermal history. The present invention is based on such a finding.

According to the present invention, there is provided a method of determining the degree of embrittlement of low alloy steel, comprising the steps of:

bringing low alloy steel into contact with an aqueous solution of an aromatic compound having a nitro group and at least one of a hydroxyl group and a carboxyl group;

measuring an open circuit potential of the steel; and determining the degree of embrittlement of the low alloy steel caused by the thermal history of the low alloy steel, using the measured value.

Aromatic compounds which can be used in the method of the present invention are as follows: nitrophenols such as o-nitrophenol, m-nitrophenol, p-nitrophenol, 2,4-dinitrophenol, 2,4,6-trinitrophenol, or 2,4,6-trinitroresorcinol; and nitrobenzoic acids such as 2,4-dinitrobenzoic acid, 3,5-dinitrobenzoic acid, 2,5-dinitrobenzoic acid, 3,4-dinitrobenzoic acid, 2,3-dinitrobenzoic acid, 2,6-dinitrobenzoic acid, o-nitrobenzoic acid, m-nitrobenzoic acid, or p-nitrobenzoic acid. The most preferable compounds are 2,4,6-trinitrophenol and 2,4-dinitrobenzoic acid.

An aqueous solution of the aromatic compound used in the method of the present invention may contain more than two of the aromatic compounds described above.

The concentration of the aqueous solution is preferably set such that it has a pH of 3.5 or less and, more preferably, a pH of 2.5 or less. Such a concentration is, e.g., 0.1 g/l to 2 g/l. When the low alloy steel is brought into contact with an aqueous solution whose pH exceeds 3.5, an oxide film or a hydroxide film tends to be formed on a surface thereof, and it is difficult to determine the degree of embrittlement of the low alloy steel.

As a result of examining a reaction mechanism of a compound which is used in the present invention, it was found that a nitro group is reduced to an amino group and, more particularly, a nitro group at a para position is reduced to an amino group.

More specifically, in the solution according to the present invention, reduction of hydronium ions, i.e., generation of hydrogen, was almost not found despite the fact that the solution is acidic. On the other hand, unlike the present invention, the degree of embrittlement caused by the thermal history of the steel cannot be determined with normal inorganic acids (e.g., sulfuric acid, perchloric acid, and hydrochloric acid) or aliphatic organic acids (e.g., acetic acid, citric acid, and oxalic acid) or aromatic compound having no nitro group (e.g., salicylic acid and phthatic acid), which causes hydrogen generation upon reaction.

As described above, according to the method of the present invention, the degree of embrittlement of low alloy steel can easily be determined simply by bringing the low alloy steel into contact with a predetermined solution and by measuring its open circuit potential. The present inventors found, by further improving the above-described method, a method which determines the degree of embrittlement of the low alloy steel with higher accuracy. More specifically, in this method, the aqueous solution of given ones of the above-described aromatic compounds is stirred prior to or immediately after immersion of the low alloy steel into the solution. After the predetermined period, the stirring is stopped, then the rate of change in the open circuit potential of the low alloy steel immediately after the stirring is stopped is measured, and the degree of embrittlement of the low alloy steel is determined by the rate of change.

The rate of change in the open circuit potential of the low alloy steel within a predetermined time period after the stirring of aqueous solution of the aromatic compound is stopped has a linear correlation with the degree of embrittlement thereof and is free of fluctuations depending on the shape and size of an electrolytic cell. Therefore, the degree of embrittlement determination can be performed with high accuracy and good reproducibility. The predetermined time period after the stirring is stopped is preferably 10 sec to 1 min depending on the temperature of the solution.

On the surface of an object to be measured, which is in contact with the above-described stirred solution, a reaction material is supplied in sufficient quantities and a substantially constant open circuit potential is detected. After the stirring of the solution is stopped, a diffusion layer is formed in the solution adjacent to the surface of the object to be measured in contact with the solution. The rate of change in the open circuit potential, which is detected when the stirring of the solution is stopped, is thought to be related with the formation rate of the diffusion layer above described, and was found to correspond to the degree of embrittlement of the object to be measured. Accordingly, the degree of embrittlement of the object can be determined by comparing the value of the rate of change in the open circuit potential thereof with a value obtained by measuring a reference low alloy steel under the same conditions.

As a method of stirring the solution, all conventional agitating methods can be used. For example, agitation by a magnetic stirrer, a rotational agitator, or a handy type mixer can be used, as well as agitation by bubbling a gas. In the last case, Ar, $N_2$, and air are suitable gases. The time required to stir the solution depends on the test area of the object or the amount of the solution. However, a few minutes to less than twenty minutes is generally sufficient.

In the method of the present invention described above, the open circuit potential of low alloy steel can be determined using only a reference electrode, and no auxiliary electrode is necessary. The reference electrode may either be directly immersed in the aqueous solution or connected using a salt bridge.

As described above, according to the method of the present invention, the degree of embrittlement of low alloy steel caused by its thermal history can be determined simply, with high accuracy, and good reproducibility. The effects are as follows.

(1) High sensitivity: There is an open circuit potential difference of 70 mV or more for a difference of 100° C. of FATT according to the type of aqueous solution. FATT is a parameter of the degree of embrittlement. In a conventional method, which artificially performs potential scanning and measurement together with formation of a passive film, a change in measured values corresponding to the degree of embrittlement is small, so that its sensitivity is low.

(2) High accuracy: According to the present invention, since measurement is performed with an oxide film on a surface of a used low alloy steel being removed, both anode and cathode reactions take place with good reproducibility, and scatters in the open circuit potential are small. In a conventional polarization method, the measurement is susceptible to slight changes in the quantity and quality of an oxide film, consequently, scatters in the measured value are large.

(3) Simplicity: Conventionally, since it is necessary to perform the potential scanning by using reference and auxiliary electrodes, besides a working electrode which is the object to be measured, both an electrolytic cell and a measuring apparatus therefore become very complex. According to the present invention, since an auxiliary electrode is not necessary because there is no need to perform potential control, both the electrolytic cell and the measuring apparatus are very simple.

According to the present invention, there is further provided an apparatus for determining the degree of embrittlement caused by the thermal history of low alloy steel, comprising an envelope which houses an aqueous solution of an aromatic compound having a nitro group and at least one of a hydroxyl group and a carboxyl group therein, an opening through which the aqueous solution contacts the low alloy steel, and a reference electrode which contacts the aqueous solution. The apparatus may further be provided with means to stir the aqueous solution.

As a means to stir the aqueous solution, a means to blow gas into the aqueous solution, an agitating blade driven by a motor, or a magnetic stirrer driven by a magnetic rotating apparatus can be used.

With this apparatus, the degree of embrittlement of an object to be measured can be determined simply by bringing the object to be measured into contact with the aqueous solution without extracting any sample therefrom.

DETAILED DESCRIPTION OF THE PREFERRED EMBODIMENTS

The present invention will now be described in detail.

First, the correlation, which is the foundation for the method of the present invention, between the open circuit potential of a low alloy steel and the degree of embrittlement thereof when the low alloy steel contacts the aqueous solution of a predetermined aromatic compound will be described.

Figure 1:
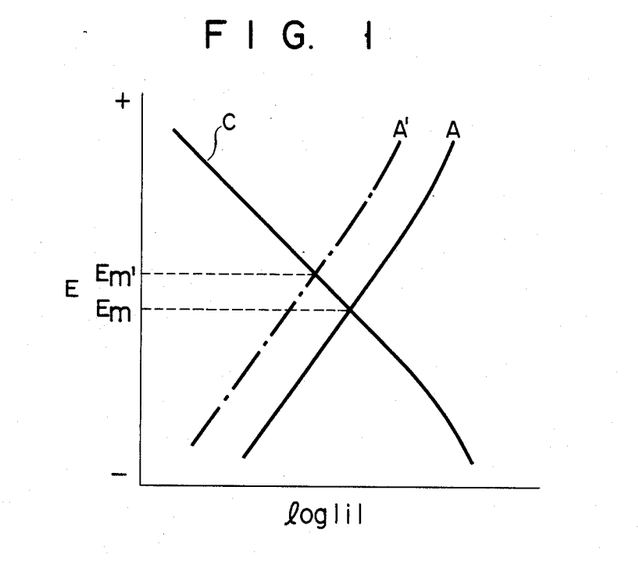
FIG. 1 is an Evans diagram showing changes in the open circuit potential of low alloy steel, which is the foundation of the method of the present invention.

FIG. 1 is an Evans diagram showing polarization behavior when a low alloy steel such as Cr-Mo steel or Cr-Mo-V steel is brought into contact with an aqueous solution of an aromatic compound having a nitrile group and at least one of hydroxyl and carboxylic groups in molecule. In the solution, the hydrogen generation reaction as in a normal acid electrolytic solution substantially did not occur in the potential region close to the open circuit potential. Reduction of a nitro group in the aromatic nitro compound as the solution component to an amino group was predominant. The reduction reaction was not influenced by the change in metal texture caused by the thermal history, so the cathode polarization curve can be represented by curve C for both the brittle and nonbrittle materials. If the anode polarization curve corresponding to the iron dissolution reaction is represented by curve A for the nonbrittle material, the open circuit potential is a mixed potential represented by Em. If this material is subjected to thermal history and embrittled, and dislocation density serving as an active point of iron dissolution is decreased, the anode polarization curve shifts from curve A to curve A'. As a result, the open circuit potential is shifted to be noble from Em to Em'. The relationship between the potential and brittlement can be obtained by using a predetermined aromatic compound characterizing the present invention. A conventional acid solution cannot provide the effect described above. The effect will be described in more detail below.

Figure 2:
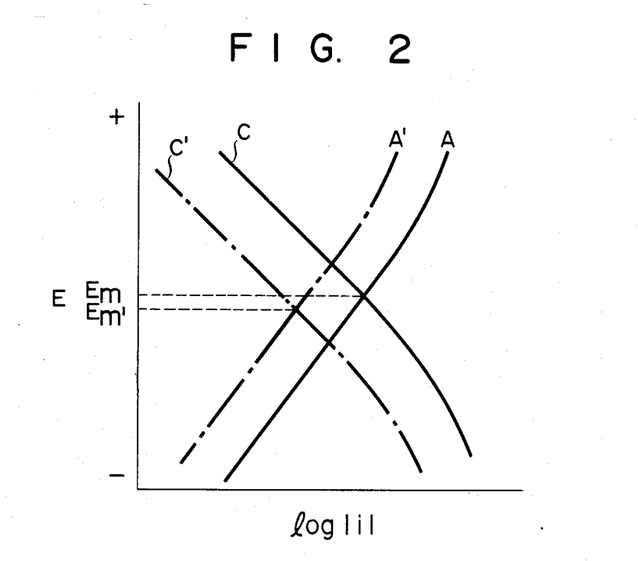
FIG. 2 is an Evans diagram showing known changes in an open circuit potential of low alloy steel in a conventional acid solution.

FIG. 2 shows an Evans diagram showing the polarization behavior of a low alloy steel in a solution of a normal inorganic acid such as hydrochloric acid, perchloric acid, or sulfuric acid, and in a solution of a normal organic acid such as acetic acid, oxalic acid, or citric acid. In such an acid solution, the cathode reaction is the reduction of hydronium ions and is represented by curve C for a nonbrittle material. When a low alloy steel is embrittled by its thermal history, the effective surface area with a low hydrogen over-voltage due to the presence of impurities (e.g., phosphorus) and a carbonate in steel is decreased by impurity segregation. As a result, the hydrogen generation rate is decreased and therefore the cathode polarization curve shifts from curve C to curve C'. The relationship concerning the iron dissolution reaction is substantially the same as that in FIG. 1. The anode polarization curves for the nonbrittle and brittle materials are represented by curves A and A', respectively. Therefore, the open circuit potential is shifted to be less noble from Em for the nonbrittle material to Em' for the brittle material. The phenomenon of a change in the open circuit potential to be less noble upon degradation in mechanical property due to heat is observed in a normal acid solution. In this case, the change in the anodic polarization curve as a result of embrittlement does not greatly differ from the change in the cathodic polarization curve, and variations in these changes adversely affect the sensitivity. Therefore, compared with the solution of the present invention, sensitivity is low and reproducibility is poor.

As can be estimated from the above mechanism, if an adsorptive material, especially a surfactant, is contained in the solution of the present invention, the reaction active points are masked. As a result, no difference between solubility of the brittle material and that of the nonbrittle material occurs, and the degree of embrittlement cannot be determined.

Examples of the present invention will now be described.

EXAMPLE 1

Figure 3:
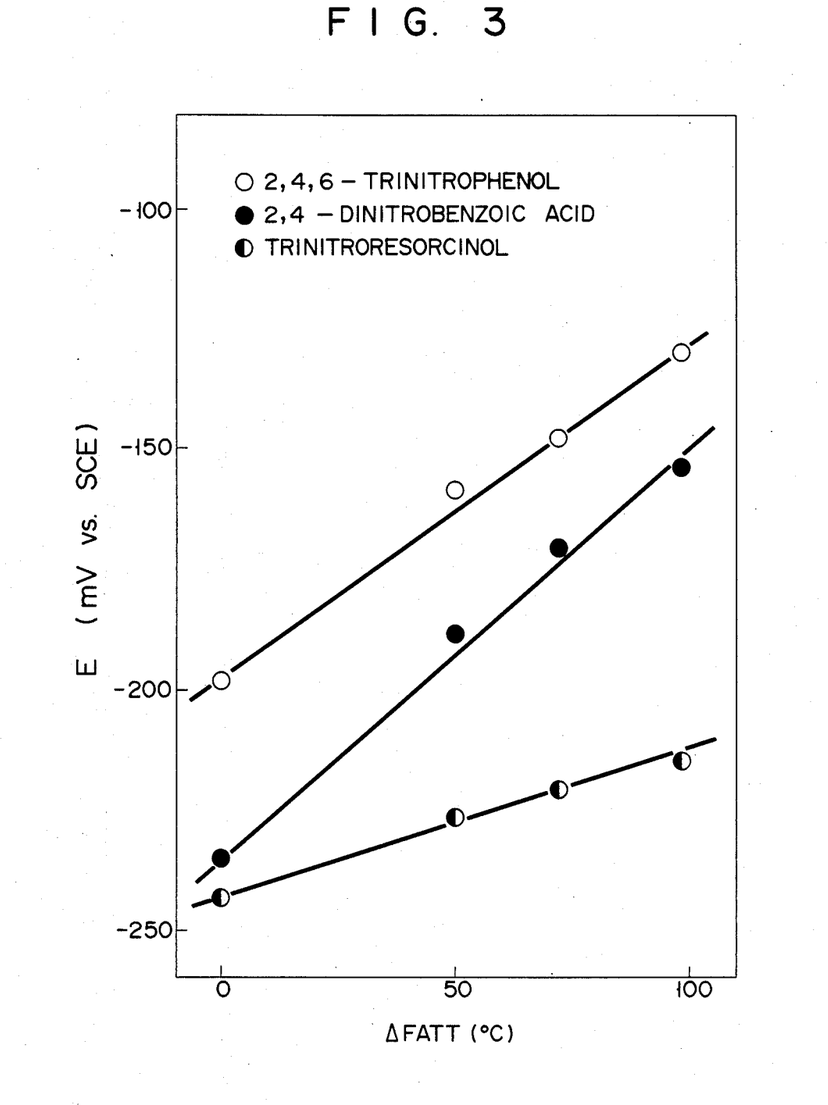
FIG. 3 is a graph, according to one embodiment of the present invention, showing a relationship between $\Delta$FATT and the open circuit potential of Cr-Mo-V steel.

2,4,6-trinitrophenol and trinitroresorcinol as aromatic compounds having hydroxyl and nitro groups, and 2,4-dinitrobenzoic acid as an aromatic compound having carboxyl and nitro groups were selected, and aqueous solutions thereof were prepared. These aqueous solutions had pHs of 2.2. Four kinds of Cr-Mo-V steel having different brittlenesses were immersed into these solutions, and the open circuit potentials thereof were measured using a saturated calomel electrode as a reference electrode. The results are shown in FIG. 3. In FIG. 3, fracture appearance transition temperature difference (ΔFATT) as a parameter for the brittleness of steel is plotted along the abscissa, and the open circuit potential is plotted along the ordinate. ΔFATT was obtained by the Charpy impact test.

As is apparent from the graph in FIG. 3, although the three solutions have different open circuit potential values and different slopes depending on brittleness, they all correspond linearly to ΔFATT, and the open circuit potential shifts to the noble side as the degree of embrittlement increases.

In the case where Cr-Mo steel instead of Cr-Mo-V steel was used as low alloy steel, the results similar to those in FIG. 3 were obtained, and the degree of embrittlement could be determined.

Control

The same measurements as those in Example 1 were performed using aqueous solutions of perchloric acid (pH 2.2), oxalic acid (pH 2.3), acetic acid (pH 3.5), and citric acid (pH 2.7). The results are shown in FIG. 4.

Figure 4:
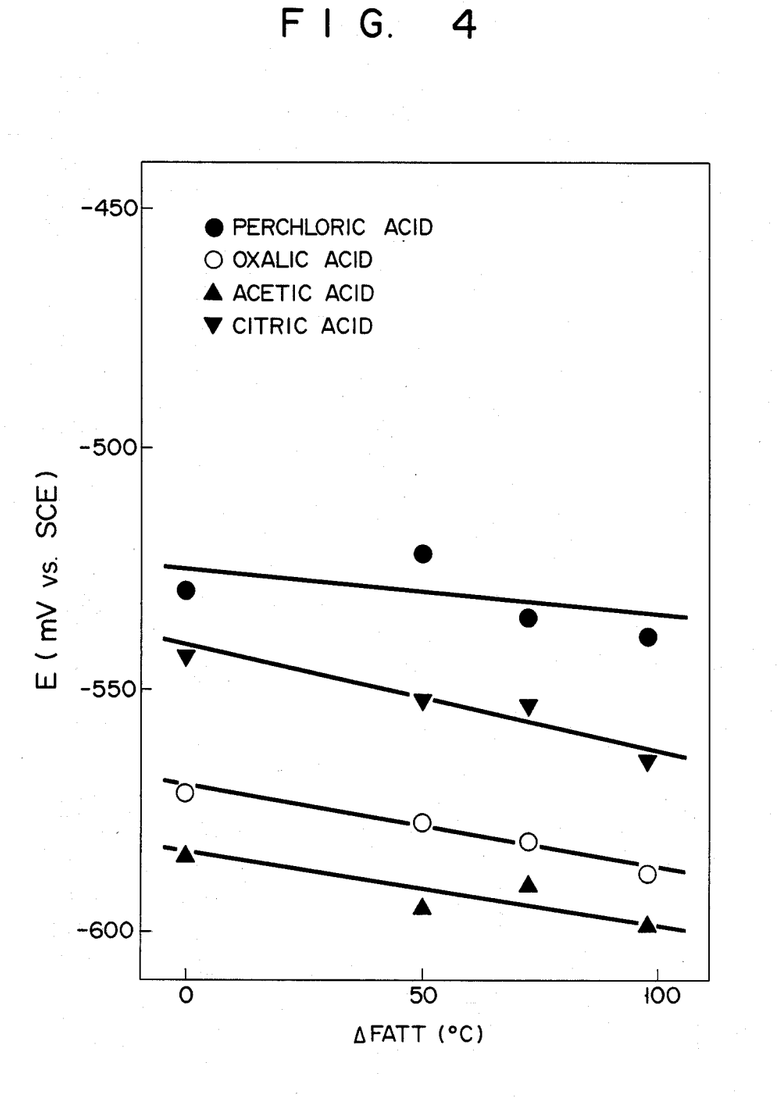
FIG. 4 is a graph, according to a comparative example of the present invention, showing the relationship between $\Delta$FATT and the open circuit potential of Cr-Mo-V steel.

As is apparent from FIG. 4, with any of these aqueous acid solutions, the open circuit potential shifts to the less noble side as the degree of embrittlement increases, but the changes therein are small while the scattering is large. Therefore, it is difficult to determine the degree of embrittlement.

EXAMPLE 2

Figure 5:
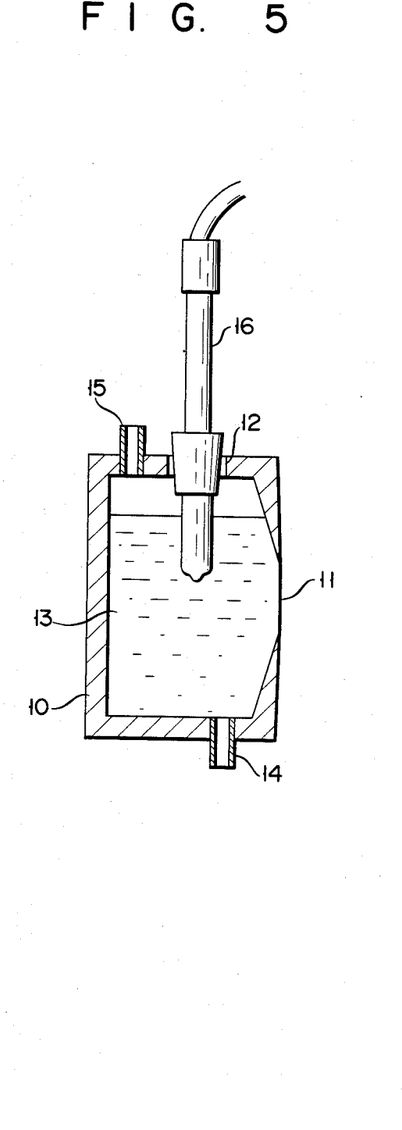
FIG. 5 is a sectional view of an electrode apparatus used in another embodiment of the present invention.

FIG. 5 is a sectional view of an electrode apparatus for determining the degree of embrittlement of low alloy steel, used in the method of the present invention.

In the electrode apparatus shown in FIG. 5, main body 10 comprises opening 11 through which low alloy steel (not shown), as an object to be measured, is brought into contact with an electrolytic solution, and through hole 12 through which reference electrode 16 is inserted. Electrolytic solution 13 is contained in body 10. A gas flows into the electrolytic solution through gas inlet 14, and is exhausted therefrom through outlet 15. Bubbling of the influent gas is controlled by a flow controller (not shown), thereby obtaining a sufficient stirring of electrolytic solution 13. Air, $N_2$, Ar and other gases can be used.

The following measurements were performed using the electrode apparatus having the above construction.

2,4,6-trinitrophenol as an aromatic compound having hydroxyl and nitro groups, and 2,4-dinitrobenzoic acid as an aromatic compound having carboxyl and nitro groups were used to prepare two types of electrolytic solutions. The concentration of each solution was set to provide a pH 2.2. Each solution was contained in the apparatus shown in FIG. 5 and was brought into contact with Cr-Mo-V steel through opening 11. Cast and forged Cr-Mo-V steels were used as the material to be measured. The solution was agitated by blowing air thereinto at a flow rate of 180 cc/min, through gas inlet 14. After agitating for three minutes, the air blowing was stopped. The variation over time of the open circuit potential of the Cr-Mo-V steel before and after the air blowing was stopped was measured with reference to the potential of the reference electrode. The measurement of the open circuit potential was performed using an electrometer and voltage recorder (not shown).

Figure 6:
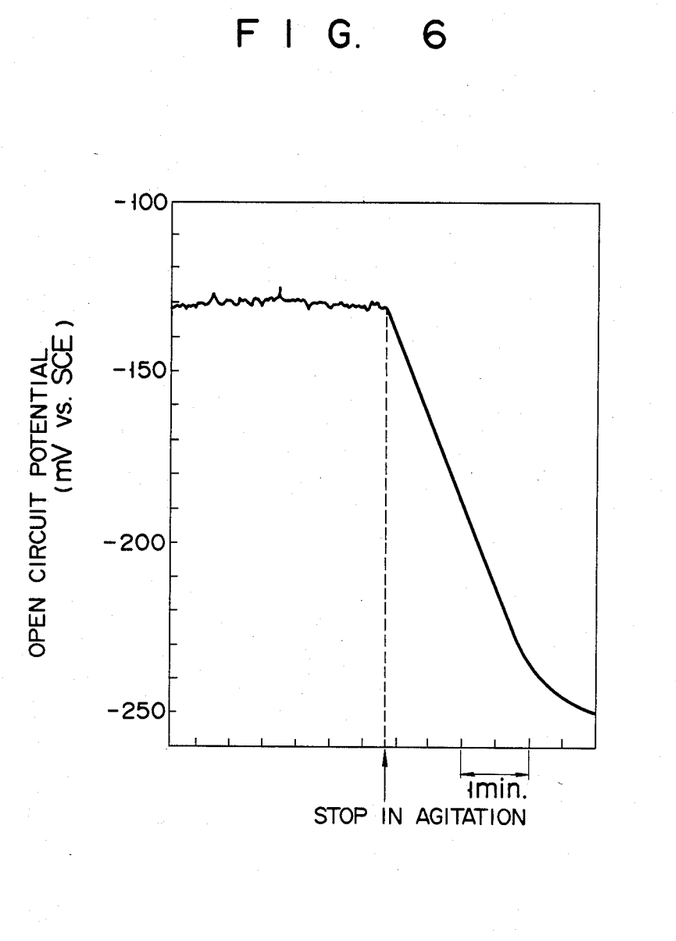
FIG. 6 is a graph showing the variation over time in the open circuit potential of Cr-Mo-V steel obtained by using the electrode apparatus shown in FIG. 5.

The measured variation over time of the open circuit potential is shown in FIG. 6. As apparent from FIG. 6, the potential is almost constant during agitation, but shifts suddenly to be less noble immediately after the agitation is stopped. Although the data shown in FIG. 6 is the data obtained using 2,4,6-trinitrophenol as the electrolytic solution, the similar result was obtained using 2,4-dinitrobenzoic acid.

Figure 7:
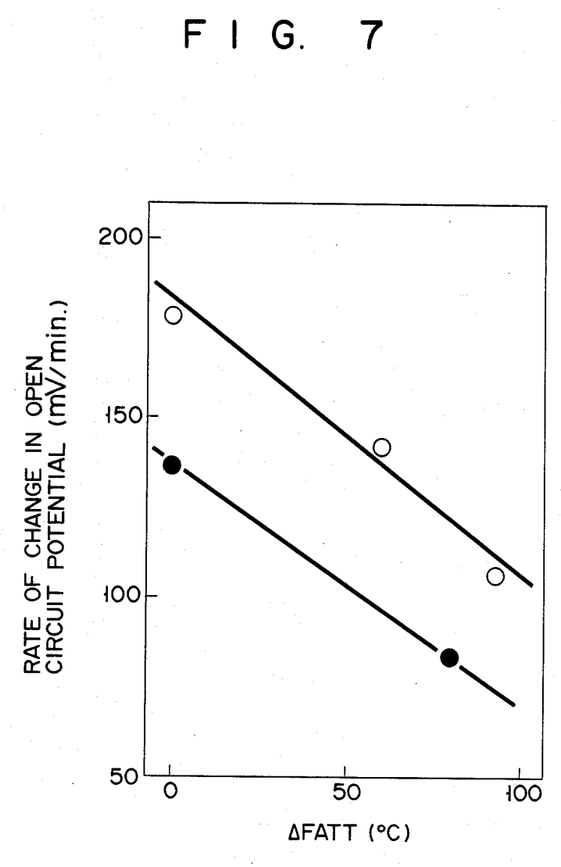
FIG. 7 is a graph, according to another embodiment of the present invention, showing a relationship between $\Delta$FATT and the open circuit potential of Cr-Mo-V steel when an aqueous solution of 2,4,6-trinitrophenol is used.
Figure 8:
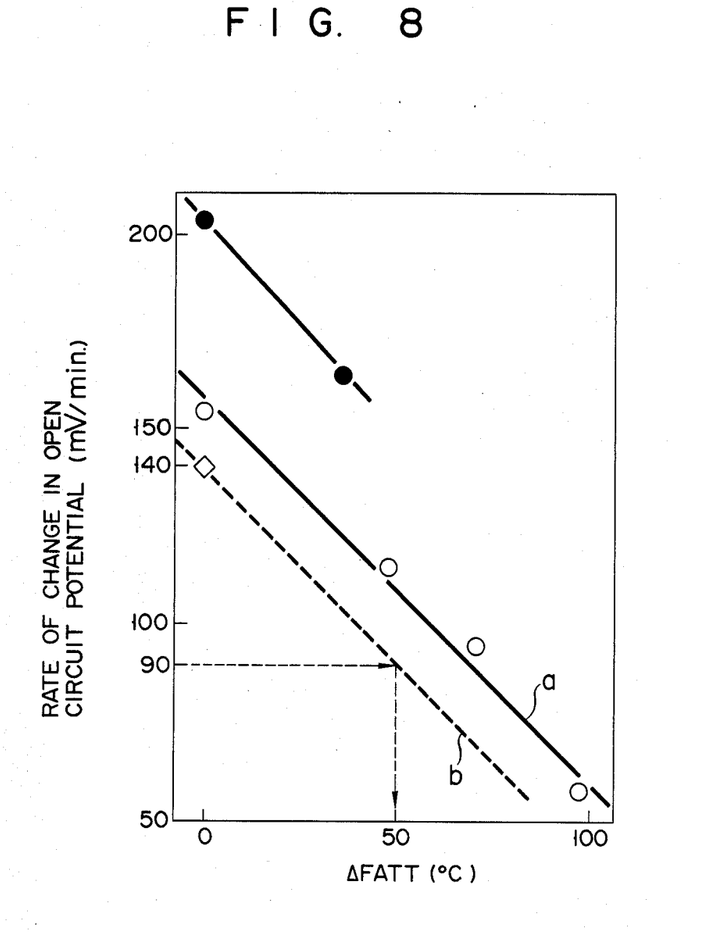
FIG. 8 is a graph, according to another embodiment of the present invention, showing the relationship between ΔFATT and the open circuit potential when an aqueous solution of 2,4-dinitrobenzoic acid is used.

An average rate of change in the open circuit potential immediately after the agitation was stopped was obtained on the basis of the measured variation over time of the open circuit potential described above. FIGS. 7 and 8 show the relationship between the average rate of change obtained in the above manner and the degree of embrittlement of the Cr-Mo-V steel. The case using 2,4,6-trinitrophenol is shown in FIG. 7, and the case using 2,4-dinitrobenzoic acid is shown in FIG. 8. In FIGS. 7 and 8, plots ○ and ● show results for forged and cast steels, respectively.

More specifically, as apparent from FIGS. 7 and 8, the absolute value of a rate of change in the open circuit potential differs when types or lots of steel are different. However, the rate of change which is relative to the reference material ($\Delta FATT=0$) is an adequate parameter for quantitatively displaying the degree of embrittlement. Therefore, the degree of embrittlement of low alloy steel as an object to be measured can be determined by comparing the rate of change in its open circuit potential with that of the reference material.

More specifically, the rate of change in an open circuit potential of a low alloy material whose degree of thermal degradation is unknown is measured using, e.g., 2,4-dinitrobenzoic acid, having the same concentration as that used in the example shown in FIG. 8, as a solution. At this time, if the rate of change at a reference portion, i.e., a portion not subjected to thermal degradation ($\Delta FATT=0$), is 140 mV/min, the reference point (shown by ◇) is determined. Therefore, broken line b, having the same slope as that of reference line a which is obtained in advance using a material of the same type and showing the relationship between the rate of change in the open circuit potential of the object to be measured and $\Delta FATT$, can be obtained. Based on broken line b, if the rate of change is, e.g., 90 mV/min at the portion which is estimated to have been subjected to thermal degradation, the degree of thermal degradation ($\Delta FATT$) at the portion can be determined to be about 50° C.

Figure 9:
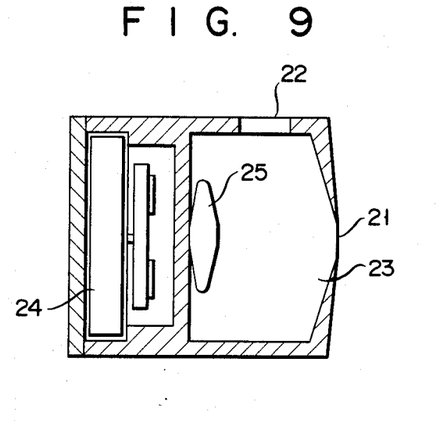
FIGS. 9 to 11 are sectional views of other electrode apparatuses.
Figure 10:
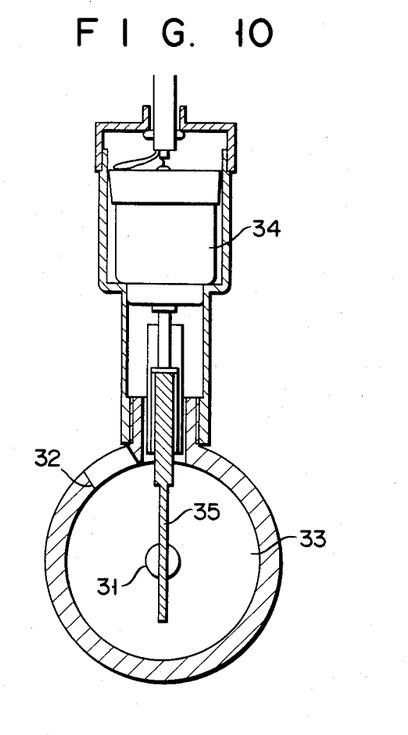
Figure 11:
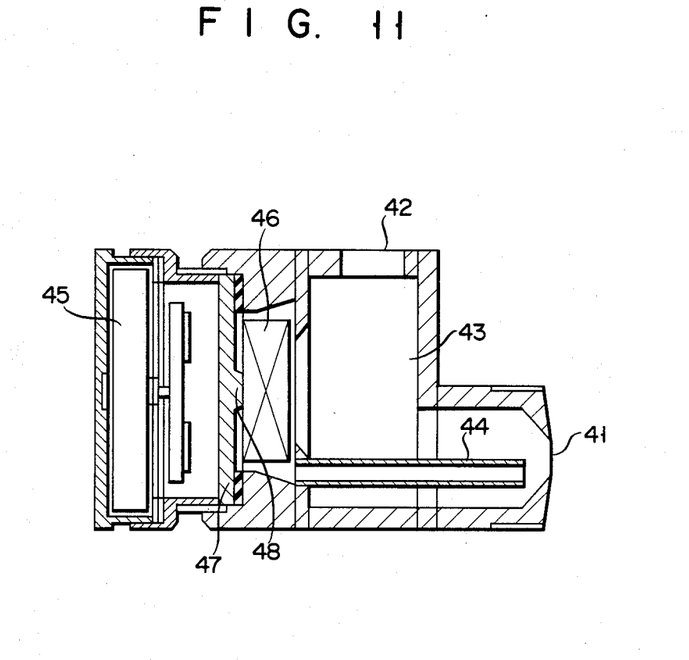

As an electrode apparatus which can be used in the present invention, the apparatuses shown in the sectional views of FIGS. 9 to 11, which are different from that in FIG. 5, can also be used. Each of these apparatuses comprises an opening (21, 31, 41) through which low alloy steel (not shown) as an object to be measured is brought into contact with a solution for measurement, and a through hole (22, 32, 42) through which a reference electrode is inserted, and contains a solution (23, 33, 43) for measurement therein, respectively. The solution is stirred or agitated by the rotation of magnetic stirrer 25 driven by magnetic rotating apparatus 24 in the apparatus of FIG. 9, and by the rotation of agitating blade 35 driven by motor 34 in the apparatus of FIG. 10. In the apparatus of FIG. 11, magnetic stirrer 46 on projection 48 of partition 47 is rotated by magnetic rotating apparatus 45, thereby introducing some of the solution in a tank to spout pipe 44 and blowing it out therefrom onto the surface of low alloy steel. In this manner, the solution is sufficiently stirred or agitated.

What is claimed is:

1. A method of determining the degree of embrittlement of low alloy steel, comprising the steps of:
   bringing the low alloy steel into contact with an aqueous solution of an aromatic compound having a nitro group and at least one of a hydroxyl group and a carboxyl group;
   measuring the value of an open circuit potential of said steel with respect to a potential of a reference electrode which is in contact with said aqueous solution; and
   determining the degree of embrittlement of said low alloy steel caused by the thermal history of said low alloy steel, using said measured open circuit value.

2. The method according to claim 1, wherein said aromatic compound is nitrophenol.

3. The method according to claim 2, wherein said nitrophenol is at least one member selected from the group consisting of o-nitrophenol, m-nitrophenol, p-nitrophenol, 2,4-dinitrophenol, 2,4,6-trinitrophenol, and 2,4,6-trinitroresorcinol.

4. The method according to claim 2, wherein said nitrophenol is 2,4,6-trinitrophenol.

5. The method according to claim 1, wherein said aromatic compound is nitrobenzoic acid.

6. The method according to claim 5, wherein said nitrobenzoic acid is at least one member selected from the group consisting of 2,4,-dinitrobenzoic acid, 3,5-dinitrobenzoic acid, 2,5-dinitrobenzoic acid, 3,4-dinitrobenzoic acid, 2,3-dinitrobenzoic acid, 2,6-dinitrobenzoic acid, o-nitrobenzoic acid, m-nitrobenzoic acid, and p-nitrobenzoic acid.

7. The method according to claim 5, wherein said nitrobenzoic acid is 2,4-dinitrobenzoic acid.

8. The method according to claim 1, wherein said aqueous solution has a concentration to provide a pH of not more than 3.5.

9. The method according to claim 8, wherein said aqueous solution has a concentration to provide a pH of not more than 2.5.

10. The method according to claim 1, further comprising the steps of stirring said aqueous solution and stopping the stirring, and wherein the measurement of the open circuit potential of said steel is performed by measuring the open circuit potential at predetermined intervals after said stirring is stopped, and the determination of the degree of embrittlement of said steel is performed using the rate of change in the open circuit potential at the predetermined intervals after the stirring is stopped.

11. An embrittlement degree detecting electrolytic solution, comprising an aqueous solution of an aromatic compound having a nitro group and at least one of a hydroxyl group and a carboxyl group, for determining a degree of embrittlement of low alloy steel, which is brought into contact with the aqueous solution, by the open circuit potential of the low alloy steel measured with respect to a potential of a reference electrode which is in contact with said aqueous solution.

12. The solution according to claim 11, wherein said aromatic compound is nitrophenol.

13. The solution according to claim 12, wherein said nitrophenol is at least one member selected from the group consisting of o-nitrophenol, m-nitrophenol, p-nitrophenol, 2,4-dinitrophenol, 2,4,6-trinitrophenol, and 2,4,6-trinitroresorcinol.

14. The solution according to claim 12, wherein said nitrophenol is 2,4,6-trinitrophenol.

15. The solution according to claim 11, wherein said aromatic compound is nitrobenzoic acid.

16. The solution according to claim 15, wherein said nitrobenzoic acid is at least one member selected from the group consisting of 2,4-dinitrobenzoic acid, 3,5-dinitrobenzoic acid, 2,5-dinitrobenzoic acid, 3,4-dinitrobenzoic acid, 2,3-dinitrobenzoic acid, 2,6-dinitrobenzoic acid, o-nitrobenzoic acid, m-nitrobenzoic acid, and p-nitrobenzoic acid.

17. The solution according to claim 15, wherein said nitrobenzoic acid is 2,4-dinitrobenzoic acid.

18. The solution according to claim 11, wherein said aqueous solution has a concentration to provide a pH of not more than 3.5.

19. The solution according to claim 18, wherein said aqueous solution has a concentration to provide a pH of not more than 2.5.

20. An apparatus for determining a degree of embrittlement which is caused by a thermal history of a low alloy steel, comprising an envelope containing therein an aqueous solution of an aromatic compound having a nitro group and at least one of a hydroxyl group and a carboxyl group, said envelope having an opening through which said aqueous solution contacts the low alloy steel, and a reference electrode which is brought into contact with said aqueous solution.

21. The apparatus according to claim 20, further comprising means for stirring said aqueous solution.

22. The apparatus according to claim 21, wherein said stirring means is means for blowing a gas into said aqueous solution.

23. The apparatus according to claim 21, wherein said stirring means is an agitating blade which is driven by a motor.

24. The apparatus according to claim 21, wherein said stirring means is a magnetic stirrer which is driven by magnetic rotating means.

* * * * *